United States Patent [19]

Schreiber et al.

[11] 4,191,952

[45] Mar. 4, 1980

[54] LOW OXYGEN FLOW ALARM FOR ANESTHESIA SYSTEMS

[75] Inventors: Peter J. Schreiber; Joachim G. M. Schreiber, both of Zionsville, Pa.

[73] Assignee: N.A.D., Inc., Telford, Pa.

[21] Appl. No.: 937,037

[22] Filed: Aug. 25, 1978

[51] Int. Cl.$^2$ ............................................. G08B 21/00
[52] U.S. Cl. .................................. 340/611; 340/506;
  340/632; 128/202.22; 128/203.14; 128/203.25
[58] Field of Search ............... 340/500, 501, 506, 543,
  340/603, 606, 611, 614, 626, 632, 52 C;
  128/184, 185, 196, 187, 208, 209, 210

[56] References Cited

U.S. PATENT DOCUMENTS

| | | | |
|---|---|---|---|
| 3,632,924 | 1/1972 | Harper | 340/52 C |
| 4,100,537 | 7/1978 | Carlson | 340/626 |
| 4,148,311 | 4/1979 | London et al. | 128/210 |

Primary Examiner—Alvin H. Waring

Attorney, Agent, or Firm—Caesar, Rivise, Bernstein & Cohen, Ltd.

[57] ABSTRACT

In anesthesia apparatus for supplying oxygen and an anesthesia gas through respective flow control valves to a patient breathing circuit a low oxygen flow alarm system is provided. The alarm system includes a restrictor in the pipeline of the oxygen flow control valve and a restrictor in the pipeline of the anesthesia gas flow control valve. A differential pressure sensing unit including a diaphragm assembly responsive to the pressure in the oxygen pipeline and another diaphragm assembly responsive to the pressure in the anesthesia gas pipeline is coupled to the restrictor pipelines. The diaphragm assemblies are opposed to each other and coupled together by a displaceable linkage. Electrical switch means are provided coupled to the linkage to provide an alarm signal when the linkage has been moved to a predetermined position indicating that the oxygen concentration has dropped below a predetermined value. The differential pressure sensing unit includes spring biasing means.

10 Claims, 5 Drawing Figures

LOW OXYGEN FLOW ALARM FOR ANESTHESIA SYSTEMS

This invention relates generally to anesthesia apparatus and more particularly to alarm systems therefore.

Anesthesia apparatus commercially available commonly include respective flow control valves for controlling the flow or supply of oxygen and anesthesia gas(es), e.g., nitrous oxide, into a common manifold and from there to a patient breathing circuit. Most apparatus also include sensing means and indicating meters, e.g., flow or rotometers, to indicate the gas flow delivered through the flow control valves as well as other system conditions, e.g., gas pressure.

It is the responsibility of the operator of the anesthesia machine to guarantee that a minimum supply of oxygen is provided in the delivered gas flow. Notwithstanding this responsibility various accidents have occurred over the past few years when the oxygen percentage decreased below a minimum safety level. Many such accidents have been a result of a failure in the oxygen supply, and inadvertent closing of the oxygen control valve or a misjudgment in the setting of the flows.

Various safety devices are known and commercially available and which respond to the pressure in the oxygen supply line. Such devices signal a decrease or total failure of the oxygen supply pressure. Such devices may also interrupt, or decrease, all gas flows other than oxygen in the event of a partial or total failure of oxygen supply pressure. However, prior art devices which function responsive to oxygen pressure have the major disadvantage that if the oxygen control valve is closed, such that no oxygen is delivered to the patient, the oxygen pressure will still exist in the supply line and the alarm device will not provide an alarm indication even though no oxygen is flowing.

Accordingly, it is a general object of the instant invention to provide an alarm system for use with anesthesia systems which overcomes the disadvantages of the prior art.

It is a further object of the invention to provide an alarm system for anesthesia systems which operates responsive to monitored oxygen flow and not oxygen pressure.

It is a further object of the instant invention to provide an alarm system for anesthesia systems which operates effectively and reliably yet is simple in construction and relatively compact.

It is still a further object of the instant invention to provide an alarm system for anesthesia systems which provides an alarm signal in the event that the oxygen concentration supplied to the patient's breathing circuit drops below a predetermined value, with the predetermined value varying inversely with total gas flow rate through the circuit so that the patient always receives a minimum absolute amount of oxygen.

These and other objects of the instant invention are achieved by providing an alarm system for use with anesthesia apparatus supplying oxygen through one pipeline into a manifold while supplying an anesthesia gas through a second pipeline into the manifold. The alarm system comprises first pressure actuated means responsive to the oxygen pressure in the first pipeline and having a first output member whose position is dependent upon said oxygen pressure, second pressure actuated means responsive to the anesthesia gas pressure in the second pipeline and having a second output member whose position is dependent upon said anesthesia gas pressure, and alarm means including displaceable means, said first and second output members being coupled to said displaceable means and acting in opposition thereon, such that said first output means tends to move the displaceable means in a first direction while said second output means tends to move the displaceable means in a second direction, said alarm means producing an alarm signal whenever said displaceable means has been moved in said second direction to a predetermined position.

Other objects and many of the attendant advantages of this invention will be readily appreciated as the same becomes better understood by reference to the following detailed description when considered in connection with the accompanying drawing wherein.

Figure 1:
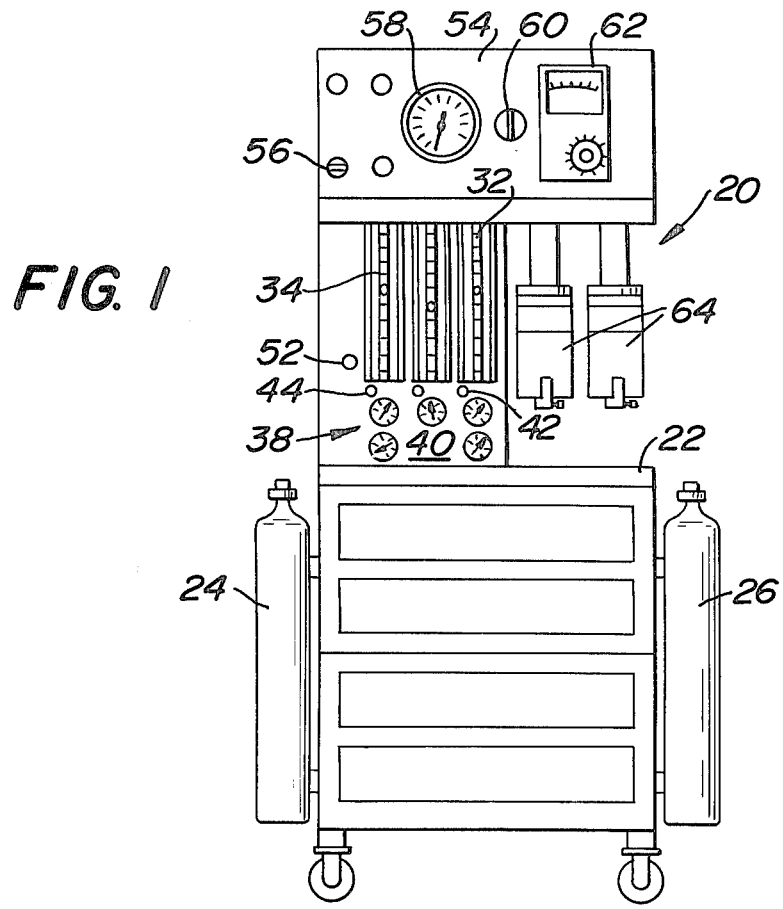
FIG. 1 is a front elevational view of an anesthesia apparatus including the alarm system of the instant invention.

Referring now to the drawings wherein like reference characters refer to like parts there is shown generally at 20 an anesthesia apparatus utilizing the low oxygen flow alarm system making up the instant invention. The anesthesia apparatus 20 shown in FIG. 1 is arranged to provide a mixture of oxygen and anesthesia gas(es) through a manifold for inhalation by the patient. The apparatus 20 basically comprises a portable cart 22 upon which are supported compressed oxygen cylinder 24 and compressed anesthesia gas cylinder 26. Oxygen and anesthesia gas, e.g., nitrous oxide, are provided via respective flow control valves 28 and 30 and respective flow meters 32 and 34 into a common manifold 36 where the gases mix for supply to the patient breathing circuit (not shown). The flow control valves establish the rate of flow of gas therethrough, while the flow meters indicate the gas flow rates. The apparatus also includes pipeline inlet connections (not shown) for use with hospital piped oxygen, nitrous oxide or other gases.

The flow control valves 28 and 30 are mounted within a centralized control panel 38 on the cart. Each valve is of conventional construction and includes an adjustment knob which is mounted on the front of the panel 38 for ease of access. The knob 42 adjusts the flow of oxygen through valve 28 while knob 44 adjusts the flow of nitrous oxide through valve 30. The flow meters 32 and 34 are also mounted on the centralized control panel, as are several gauges 40 for indicating various system conditions, e.g., gas cylinder content, etc.

Figure 2:
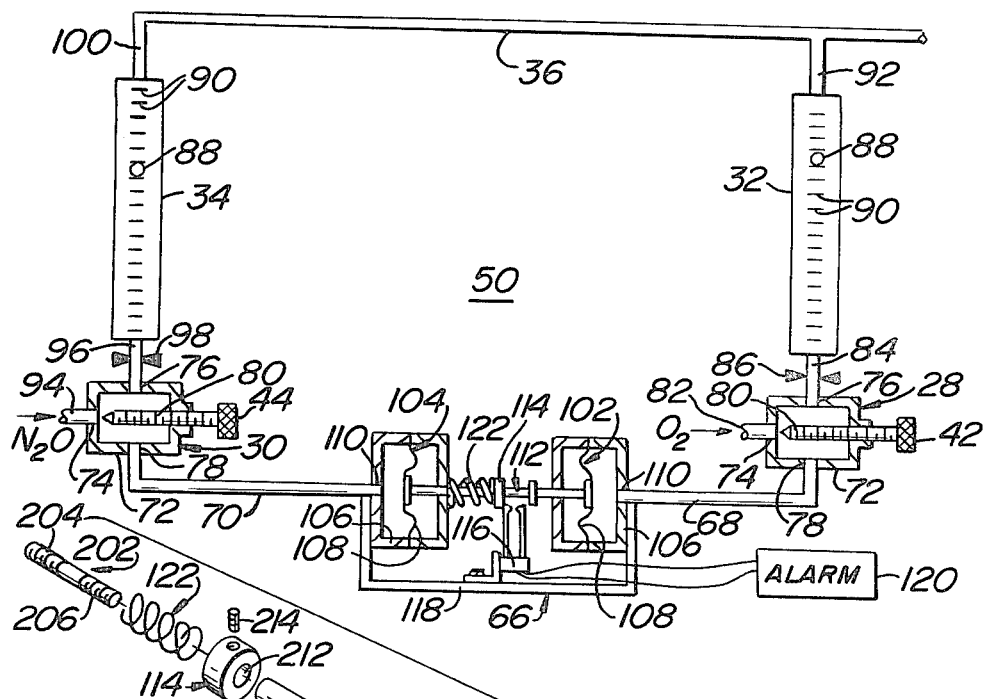
FIG. 2 is a schematic diagram of the alarm system included in the apparatus of FIG. 1.

The low oxygen flow alarm system forming the instant invention is shown schematically by the reference numeral 50 in FIG. 2 and is mounted within the panel 38 of apparatus 20. The system 50 includes, among other things to be described in detail later, an indicator lamp 52, mounted on the front face of the panel 38, which lights whenever the flow of oxygen drops below a predetermined value.

A display and control panel 54 is mounted above the alarm panel 38. The panel 54 includes a main switch 56 for actuating all oxygen supply failure devices, a sphygmomanometer 58, a ventilation pressure monitor 60 and an oxygen analyzer 62. A pair of vaporizers 64 for Halophane and Enflurane are mounted below the control panel 54.

Referring now to FIG. 2 it can be seen that the low oxygen alarm system 50 of the instant invention basically comprises differential pressure sensing means 66. The differential pressure sensing means 66 will be described in detail later, suffice for now to state that it is arranged to monitor the oxygen pressure in the pipeline feeding the oxygen to the common manifold while also monitoring the nitrous oxide pressure in the pipeline feeding it to the common manifold. Thus the differential pressure sensing means 66 includes a first diaphragm which is pressurized, via a pilot pipeline 68 from the oxygen flow control valve 28, and a second diaphragm which is pressurized, via a pilot pipeline 70 from the nitrous oxide flow control valve 30. As noted heretofore both flow valves 28 and 30 are of conventional construction and each includes a housing 72 having a gas inlet port 74, a gas outlet port 76, a pilot line port 78 and an adjustable needle valve element 80. The knob 42 is connected to the needle element 80 of valve 28 for adjusting the rate of oxygen flow through the valve. Similarly, the knob 44 is connected to the needle element of valve 30 for adjusting the nitrous oxide flow therethrough. A pipeline 82 is connected to port 74 of valve 28 to carry oxygen from tank 24 to the valve for distribution to its outlet port 76. The pilot pipeline 68 is connected between the pilot port 78 and the oxygen pressure sensing portion of the differential pressure sensing means 66. An outlet pipeline 84 is connected between the outlet port 76 and the bottom of the flow meter 32. A reduced orifice, linear restrictor or resistor 86, shown schematically in FIG. 2, is mounted in pipeline 84 between the flow control valve 28 and the flow meter 32.

The flow meter 32 is of conventional construction and comprises a tapered glass tube having a gradually increasing inside diameter in the upward direction. The glass tube contains a free moving float 88 which serves as an indicator of the rate of gas flow through the tube. The tube is graduated at 90 in terms of volume per unit time. The upper end of the flow meter tube 32 is connected to a branch pipeline 92 which forms the oxygen input to the common manifold 36.

The inlet port 74 of flow control valve 30 is connected to a pipeline 94 which supplies the nitrous oxide gas from the tank 26. The pilot pipeline 70 is connected between the pilot port 78 of the valve 30 and the nitrous oxide pressure sensing portion of the differential pressure sensing means 66. An outlet pipeline 96 is connected to the outlet port 76 of valve 30 and to the bottom of the flow meter 34. Flow meter 34 is of identical construction to flow meter 32. A reduced orifice, linear restrictor or resistor, shown schematically by the reference numeral 98, is connected in the outlet pipeline 96 between the flow control valve 30 and the flow meter 34. The upper end of the flow meter 34 is connected to a branch line 100 which serves as another input to the common manifold 36.

The system 50 is arranged to monitor the percentage of oxygen in the oxygen-nitrous oxide mixture and to provide an indication when the oxygen concentration drops below a predetermined value. To insure that the patient always receives an adequate absolute amount of oxygen, the predetermined value varies inversely with the total fresh gas (mixture) flow rate, as will be described in detail later. The oxygen concentration is monitored by comparing the ratio of the oxygen flow and the nitrous oxide flow into the fresh gas manifold 36. This is accomplished by comparing the oxygen pressure and the nitrous oxide pressure that result from the flow of such gases through restrictors 86 and 98, respectively.

As will be appreciated by those skilled in the art the resulting pressures within the housings of valves 28 and 30 are each a function of the resistance of the associated restrictor and the gas flow through the restrictor. In general, this relationship is not linear, but an increase in flow always produces an increase in pressure. Consequently, the ratio of oxygen pressure to the nitrous oxide pressure is related to the oxygen concentration in the manifold 36.

The pressure ratio is monitored by the differential pressure sensing means 66. The sensing means 66 basically comprises a switch in the form of two isolated pressure sensing units 102 and 104 to insure that the oxygen and the nitrous oxide gases are kept separate. The pressure sensing unit 102 basically comprises an enclosure 106 having a diaphragm 108 disposed therein. The enclosure 106 includes a pilot port 110 to which the pilot pipeline 68 is connected. The unit 104 is identical in construction to unit 102 and has its pilot port 110 connected to pilot pipeline 70.

The diaphragm assemblies 108 of units 102 and 104 are connected together by a mechanical linkage assembly 112 which is arranged in such a manner that the movement of the diaphragm assembly 108 of unit 102 in response to the oxygen pressure opposes the movement of the diaphragm assembly 108 of unit 104 which operates in response to the nitrous oxide pressure. Since the pressure of the oxygen in pilot pipeline 68 and the nitrous oxide in pilot pipeline 70, depend not only on the oxygen and nitrous oxide gas flows, respectively, through the respective control valves 28 and 30, but also on the values of the corresponding resistances of the restrictors 86 and 98, respectively, the values of the resistances are selected in such a manner that a point on the linkage assembly 112 moves past a stationary reference point when the ratio of the oxygen flow to the nitrous oxide flow (and consequently the oxygen concentration in the fresh gas) just exceeds or falls below a predetermined value. The value is referred to hereinafter as the switch point ratio. A stop element 114 establishes the reference point on the linkage assembly 112 while a leaf spring electrical switch establishes the fixed reference point. To that end the switch 116 is fixedly mounted on a frame 118 mounting the units 102 and 104. An alarm circuit 120 is connected to the switch 116 and includes the indicator lamp 52 described heretofore and which is mounted on the centralized alarm panel 38.

As will be appreciated from the foregoing, movement of the linkage assembly 112 and hence stop 114 to the right of the position shown in FIG. 2 causes the contacts of switch 108 to close. This action energizes the alarm circuit 120 which effects the illumination of the lamp 52 to indicate that the oxygen concentration has dropped below the critical value.

In accordance with a preferred aspect of this invention it is desirable that the switch point ratio vary inversely with respect to the fresh gas flow rate to insure that at lower total gas flows a higher percentage of oxygen is provided into the manifold 36, to thereby insure that the patient always gets a minimum absolute amount of oxygen. To accomplish this, the linkage assembly 112 includes biasing means, preferably in the form of a helical compression spring 122. The spring is mounted on the linkage assembly between the stop 114 and the enclosure 106 of unit 104 so that its force opposes the force produced by the diaphragm assembly 108 of unit 102 in response to the sensed oxygen pressure.

Since the deflection of the spring 122 at the switch point is always the same, the spring force is a constant and the oxygen concentration is above the critical value only when the force due to the oxygen flow exceeds the force due to the nitrous oxide flow plus the force of the spring. At low flows, the forces due to the flows are small compared to the spring force, and the switch point ratio is high. Conversely, at high flows, the spring force is relatively insignificant and the switch point ratio approaches that determined by the selection of the conductances of the resistors 86 and 98.

The following mathematical model demonstrates the operation of the differential pressure sensing means 66. In the model, the restrictors 86 and 98 are assumed to be linear and the active area of the diaphragm assembly of each unit 102 and 104 is the same.

The switch point ratio is attained when the linkage assembly 112 is in static equilibrium and defined by the following formula:

$$F_{O2} = F_{N2O} + F_s \qquad (1)$$

where $F_{O2}$ is the force produced by the unit 102 diaphragm assembly 108 due to the oxygen pressure in pilot line 68, $F_{N2O}$ is the force produced by the unit 104 diaphragm assembly 108 due to the nitrous oxide pressure in pilot line 70 and $F_s$ is the force produced by the compression of the spring 122.

As is known, the force produced on a diaphragm is equal to the pressure on the diaphragm multiplied by the area thereof. Accordingly:

$$F_{O2} = P_{O2} \cdot A_{O2} \qquad (2)$$

$$F_{N2O} = P_{N2O} \cdot A_{N2O} \qquad (3)$$

where $P_{O2}$ is the pressure produced on the unit 102 diaphragm 108 due to the oxygen flow through the restrictor 86, $P_{N2O}$ is the pressure on the unit 104 diaphragm 108 due to the nitrous oxide flow through the restrictor 98, $A_{O2}$ is the area of the unit 102 diaphragm and $A_{N2O}$ is the area of the unit 104 diaphragm. Since the resistrictors 86 and 98 are linear the pressure produced on each unit's diaphragm is equal to the resistance of the associated restrictor multiplied by the gas flow therethrough. Accordingly:

$$P_{O2} = R_{O2} \cdot Q_{O2} \qquad (4)$$

$$P_{N2O} = R_{N2O} \cdot Q_{N2O} \qquad (5)$$

where $R_{O2}$ is the resistance of the restrictor 86, $R_{N2O}$ is the resistance of the restrictor 98, $Q_{O2}$ is the oxygen flow and $Q_{N2O}$ is the nitrous oxide flow, in the mathematical model and in the preferred embodiment of the invention shown herein.

Since the area of the diaphragms of both units 102 and 104 are equal, using formulas (1)-(5) it can be seen that oxygen flow $Q_{O2}$ is defined by the following formula:

$$Q_{O2} = \frac{R_{N2O}}{R_{O2}} Q_{N2O} + \frac{F_s}{R_{O2} \cdot A_{O2}} \qquad (6)$$

As should thus be appreciated at low flows that is, when the nitrous oxide flow approaches zero, the concentration of oxygen is largely dependent on the parameter $$\frac{F_s}{R_{O2} \cdot A_{O2}}.$$

At higher gas flows, $Q_{N2O}$ is large, $$\frac{F_s}{R_{O2} \cdot A_{O2}}$$

is insignificant and the oxygen concentration is defined by the term $$\frac{R_{N2O}}{R_{O2}} Q_{N2O}.$$

This effect ensures an increasing value for the switch point ratio with decreasing flow rates. As can be seen, when the nitrous oxide flow is zero, a minimum amount of oxygen flow still occurs, which is defined by the term $$\frac{F_s}{R_{O2} \cdot A_{O2}}$$

to maintain equilibrium. This ensures that the patient receives a minimum amount of oxygen even when receiving no anesthesia gas.

Figure 4:
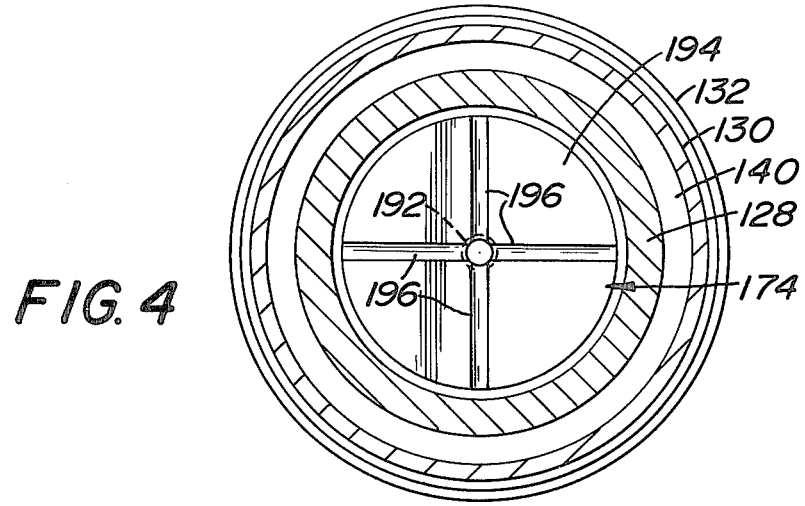
FIG. 4 is a sectional view taken along the line 4—4 of FIG. 3.
Figure 5:
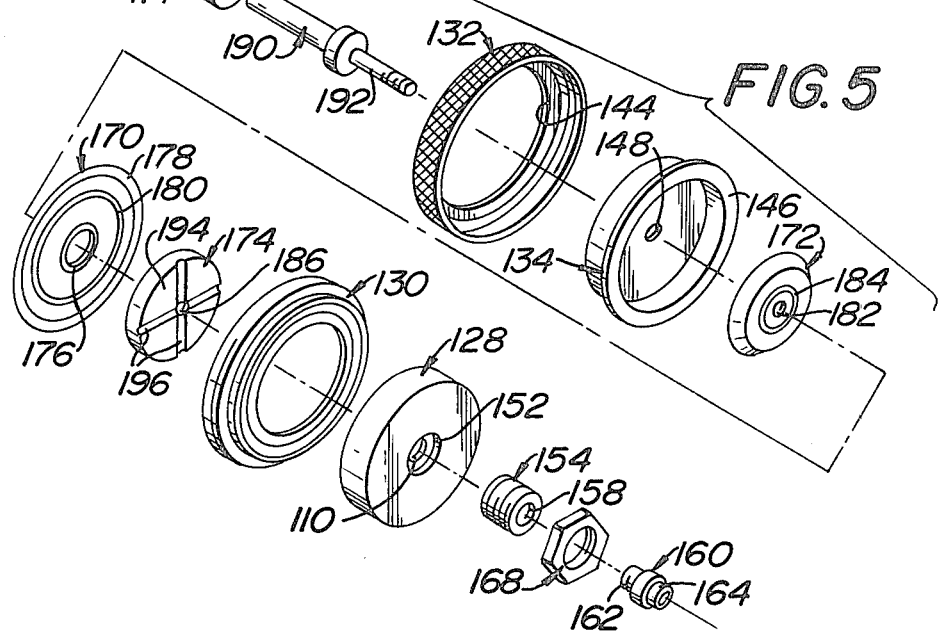
FIG. 5 is an exploded perspective view of a portion of the differential pressure switch shown in FIG. 3.
Figure 3:
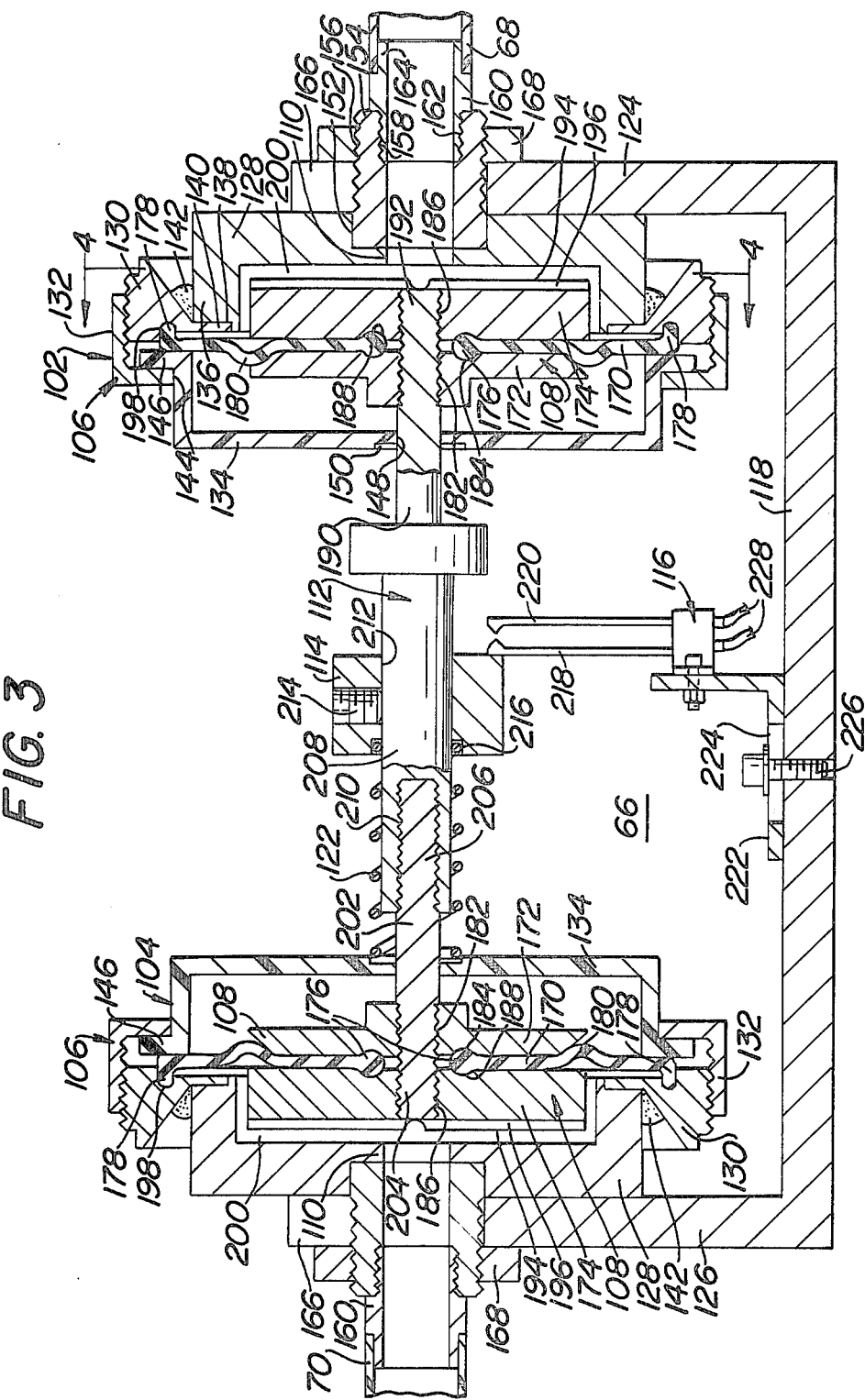
FIG. 3 is a side elevational view, partially in section, of a differential pressure switch forming a portion of the system shown in FIG. 2.

The structural details of the differential pressure sensing means 66 are shown most clearly in FIGS. 3, 4 and 5. Referring now to FIG. 3 it can be seen that the frame 118 is a generally U-shaped member having an upstanding leg 124 for supporting the sensing unit 102 and an opposed upstanding leg 126 for supporting the sensing unit 104.

Since the units 102 and 104 are of identical construction only the details of unit 102 will not be described in the interest of brevity. As can be seen the housing 106 for unit 102 is formed of an assembly of components, namely, a housing base 128, an exteriorly threaded ring 130, a knurled, interiorly threaded ring 132 and a housing cap 134. The housing base is a cylindrical member having a sidewall 136 including a ledge 138 therein. A flange 140 of the threaded ring 130 is received on the ledge and the housing base and threaded ring are connected together via a brazed joint 142. The knurled ring 132 is threadedly engaged on the ring 130 and includes a central opening 144 through which the housing cap 134 extends. The housing cap is a disc-like member having a peripheral flange 146. The central portion of the cap 134 includes an opening 148 and an annular recess 150 extends about the opening 148. The housing base 128 includes a central opening which defines the pilot pipeline input port 110. An enlarged mouth surrounds port 110. A threaded fitting or nipple 154 is permanently secured in mouth 152. The nipple 154 includes an outer threaded portion 156 and an interior threaded portion 158. A fitting 160, having a threaded end 162 is screwed into the threaded hole 158 of nipple 154. The fitting 160 includes a central opening which communicates through the hollow interior of the nipple 154 with port 110. The opposite end of the fitting 160 includes a recessed shoulder 164 for securement within the end of the pilot pipeline 68.

In order to mount the unit 106 the upstanding arm 124 includes a slot 166 through which the nipple 154 extends. A lock nut 168 is threadedly engaged on the nipple and when tightened grips the surfaces of the upstanding arm 124 contiguous with the slot 166 between it and the outside of the housing base 128.

The diaphragm assembly 108 is disposed within the hollow interior of the housing 106. The diaphragm assembly 108 comprises a flexible, resilient material, e.g., silicone rubber, diaphragm 170, a front plate 172 and back plate 174. The diaphragm 170 is a generally disc-shaped member having a central opening whose edge is in the form of an enlarged bead 176. The outer periphery of the diaphragm 170 is also in the form of a bead 178. The medial portion of the diaphragm is in the form of an offset annularly extending depression which is concentric with the central opening of the diaphragm and the outer periphery thereof. The portion of the diaphragm between the recess 180 and the internal bead 176 is tightly held between the front plate 172 and back plate 174.

As can be seen in FIGS. 3 and 5 the front plate is a disc-like member having a threaded central opening 182. The rear surface of the front plate 172 includes an annularly extending recess 184 in which the peripheral bead 176 of the diaphragm 170 is disposed. The periphery of the front plate 172 tapers from the rear wall to the front wall to accommodate the offset portion of the diaphragm forming the recess 180. The back plate 174 is a disc-like member having a centrally threaded opening 186 aligned with opening 182 in the front plate 172. The front or inner surface of the back plate 174 includes an annular groove 188 to accommodate the peripheral bead 176 of the diaphragm 170. The front plate 172, diaphragm 170 and rear plate 174 are secured together to form the diaphragm assembly by a threaded connecting rod 190. The connecting rod 190 forms one portion of the linkage means 112. As can be seen in FIGS. 3 and 5 the threaded rod 190 includes a threaded end 192 extending through threaded opening 182 in front plate 172, the central opening in the diaphragm and through threaded opening 186 in the back plate 174. The rear surface 194 of the back plate 174 includes four radially extending grooves 196 (FIGS. 4 and 5). The function of the grooves will be set forth later. The outer peripheral bead 178 of the diaphragm 170 is disposed within an annular recess 198 in the threaded ring 130. When the knurled ring 132 is tightened on the threaded ring 130 the bead 178 is tightly seated in the groove 198 by the force applied to the bead from the flange 146 of the cap 134. This action tightly holds the outer peripheral portions of the diaphragm in the housing 106.

The location and securement of the diaphragm assembly within the housing 106 forms a operating chamber 200 within the housing 106 and between the diaphragm assembly 108 and the interior surface of the housing base 128. The inlet port 110 communicates with chamber 200. Accordingly, the pressure existing in the pilot pipeline 68 results in the concomitant pressurization of chamber 200. This action causes the diaphragm assembly to move to the left from the position shown in FIG. 3 in accordance with the force produced by the pressurization.

As will be appreciated by those skilled in the art the radially extending channels 196 of the back plate serve to equalize the pressure on the diaphragm within chamber 200 when the diaphragm assembly is in the position where the rear surface 194 of the back plate 174 is close to the inside surface of the housing base 128.

As noted heretofore the unit 104 is of identical construction to the unit 102 except that the diaphragm assembly 108 of unit 104 is secured together by a threaded rod 202 and not rod 190. The threaded rod 202 is an elongated member having a first threaded end 204 extending through the threaded openings 182 and 186 in plates 174 and 172, respectively, and a second threaded end 206. The rod 204 forms another element of the linkage assembly 112.

The linkage assembly 112 comprises rods 190 and 202 and stop 114. As can be seen in FIGS. 3 and 5 the rod 190 includes an enlarged diameter end 208 extending opposite to the threaded end 192. The enlarged end 208 includes a threaded central bore 210. The threaded end 206 of rod 202 is screwed into bore 210 to secure rod 202 to rod 190.

The stop 114 is a collar-like element having a central opening 212 through which rod portion 208 extends. The collar 114 includes a radially extending threaded opening in which a set screw 214 is located. The collar or stop 114 can be located at any longitudinal position along rod 208 and locked in place at said position by the tightening of set screw 214 to establish the switch point on the linkage.

The spring 122 is a helical, compression spring and is disposed on rod 190 about the rearmost portion 208 thereof and about the midportion of rod 202. The spring 122 is interposed between the housing cap 134 of unit 104 and the sliding stop 114. The end portion of the spring furthest from the unit 104 is located within an annular groove 216 in one face of the stop 114 contiguous with the opening 212 therein.

The electrical switch 116 is shown clearly in FIGS. 2 and 3 and comprises a pair of leaf spring contacts 218 and 220 which extend toward the linkage assembly 112. The switch 116 is mounted on the frame 118 by a bracket 222. The bracket includes a longitudinally extending slot 224 through which a locking bolt 226 extends. Accordingly, the position of the bracket, and hence the switch 116, can be adjusted along the linkage means by the loosening of bolt 226 and the sliding of the bracket 222 parallel to the axis of the linkage 112. The bolt 226 is then tightened to lock the switch 116 in place with respect to the linkage 112. A pair of electrical conductors 228 are connected between the switch contacts 218 and 220 and the alarm means 120.

Operation of the system 50 is as follows: As long as the ratio of the oxygen pressure to the nitrous oxide pressure is greater than the switch point ratio, there by indicating that the concentration of oxygen in the gas mixture in the manifold 36 is at least at a minimum predetermined value for the existing total gas flow, the force applied to the linkage assembly 112 by the diaphragm assembly of the oxygen pressure sensing unit 102 exceeds the opposed force applied to the linkage assembly by the spring 122 and the diaphragm assembly of the nitrous oxide pressure sensing unit 104. In this condition the stop 114 is positioned to the left of the switch 116 as shown in FIG. 3 so that the contacts 218 and 220 are electrically isolated, whereupon the alarm indicator lamp 52 is off. In the event that the ratio of the oxygen pressure to the nitrous oxide pressure falls below the set point value, as could occur if the nitrous oxide flow control valve 30 is opened too much or the oxygen flow control valve 28 is closed too much, the force applied to the linkage assembly 112 by the sensing unit 104 and the spring 122 overcomes the opposed force thereon, so that the assembly quickly moves to the right from the position shown in FIG. 3. This action causes the stop 114 to move into contact with the leaf spring contact 218, whereupon the spring contacts 218 and 220 are brought into engagement to complete the alarm circuit. The completion of the alarm circuit effects the illumination of the indicator lamp 52 to warn the operating personnel of the low oxygen flow condition.

As noted heretofore and as should now be appreciated by those skilled in the art, at low total gas flows the forces produced on the linkage assembly 112 by the oxygen pressure sensing unit 102 and the nitrous oxide pressure sensing unit 104 are small as compared to the force applied to the linkage by the spring 122. Thus the switch point ratio is high and a greater concentration of oxygen must be supplied to the patient than would otherwise be necessary at higher flows. The increasing switch point ratio for decreasing flows, as established by the spring, is of considerable importance to insure that the patient always receives a minimum absolute amount of oxygen. At high flows the force produced on the linkage by the spring is insignificant compared to the forces produced by the pressure sensing units 102 and 104. Under such conditions the switch point ratio approaches the value which is established by the resistances of the restrictors 86 and 98.

It has been found that by selecting restrictors 86 and 98 to have resistances which produce a switch point concentration of approximately 30 percent at high total gas flows, e.g., 13,000 cc/min, and selecting a spring having a biasing effect to produce a set point ratio of approximately 80 percent at low total gas flows, e.g., 500 cc/min, a viable and safe alarm system is provided.

It must be pointed out at this juncture that the low oxygen flow alarm system of the instant invention is not limited to any particular anesthesia apparatus or equipment and can be used with any gas system providing at least two gases into a manifold, where a predetermined concentration of one gas in the mixture must be insured.

Accordingly, the alarm system 50 of the instant invention is just as useful in anesthesia systems providing oxygen, an anesthesia gas and other gases, e.g., air, to the patient. In fact the apparatus 20 shown in FIG. 1 is arranged to provide oxygen, nitrous oxide (or another anesthesia gas), as well as air to the patient breathing circuit.

Furthermore, the differential pressure sensing means of the alarm system of this invention need not be constructed as shown in the drawings herein but may utilize oxygen and anesthesia gas pressure sensing units which are not opposed to each other and connected by rigid, linear linkage means. In this regard a separate oxygen pressure sensing unit and separate anesthesia gas sensing unit can be positioned at different locations along a pivoting lever, with the oxygen pressure sensing unit tending to move the lever in one direction and the anesthesia gas sensing means tending to move it in the opposite direction. In such a system electrical switch means are coupled to the lever to provide an alarm signal when the lever is moved to a predetermined position indicating that the oxygen concentration is below the switch point ratio. The position of either sensing unit may be adjusted along the lever to permit switch point adjustment. In addition springs, weights or other biasing means can be utilized in combination with the lever.

Furtherstill, nonlinear restrictors can be used in the alarm system of the instant invention in lieu of the linear restrictors shown and described to effect the variance of the set point ratio with changing flows.

As will be appreciated from the foregoing the low oxygen flow alarm system of the instant invention is simple in construction and provides an effective means for providing a warning signal in the event that the flow of oxygen drops below a predetermined value. In addition the system takes into account the need for higher oxygen concentrations in the gas supply at lower total gas flows, thereby ensuring patient safety.

Without further elaboration, the foregoing will so fully illustrate our invention that others may, by applying current or future knowledge, readily adapt the same for use under various conditions of service.

What is claimed as the invention is:

1. An alarm system for use with anesthesia apparatus supplying oxygen through one line into a manifold while supplying an anesthesia gas through a second line into the manifold, said alarm system comprising first pressure actuated means responsive to the oxygen pressure in said first line and having a first output member whose position is dependent upon said oxygen pressure, second pressure actuated means responsive to the anesthesia gas pressure in said second line and having a second output member whose position is dependent upon anesthesia gas pressure, and alarm means including displaceable means, said first and second output members being coupled to said displaceable means and acting in opposition therein, such that said first output means tends to move the displaceable means in a first direction while said second output means tends to move the displaceable means in a second direction, said alarm means producing an alarm signal wherever said displaceable means has been moved in said second direction to predetermined position.

2. The alarm system of claim 1 wherein said first line includes a first restrictor therein and wherein said second line includes a second restrictor therein.

3. The alarm system of claim 2 wherein said first pressure actuated means comprises a first moveable diaphragm, said second pressure actuated means comprises a second moveable diaphragm and said displaceable means comprises linkage means interconnecting said first and second diaphragms.

4. The alarm system of claim 3 including fixed force biasing means acting in opposition to said first moveable diaphragm.

5. The alarm system of claim 4 wherein said biasing means comprises a spring.

6. The alarm system of claim 5 wherein said alarm system additionally comprises a switch located at said predetermined position.

7. The alarm system of claim 6 wherein said linkage means comprises adjustable stop arranged to actuate said switch when said linkage means has been moved to said predetermined position.

8. The alarm system of claim 7 wherein said switch is an electrical switch.

9. The alarm system of claim 8 additionally comprising illuminating means for producing said alarm signal.

10. The alarm system of claim 5 wherein said restrictors are linear.